United States Patent [19]

Horan et al.

[11] Patent Number: 4,859,584
[45] Date of Patent: Aug. 22, 1989

[54] CELL GROWTH RATE DETERMINATION BY MEASUREMENT OF CHANGES IN CYANINE DYE LEVELS IN PLASMA MEMBRANES

[75] Inventors: Paul K. Horan, West Chester; Bruce D. Jensen, King of Prussia; Sue E. Slezak, Downingtown, all of Pa.

[73] Assignee: SmithKline Beckman Corporation, Philadelphia, Pa.

[21] Appl. No.: 925,429

[22] Filed: Oct. 31, 1986

[51] Int. Cl.$^4$ .......................... C12Q 1/02; C12Q 1/18
[52] U.S. Cl. ...................................... 435/29; 424/7.1; 424/9; 435/32; 435/240.2; 436/63; 436/172
[58] Field of Search ................ 435/2, 29, 32; 424/7.1, 424/9; 436/63, 172

[56] References Cited

U.S. PATENT DOCUMENTS

| | | | |
|---|---|---|---|
| 4,168,206 | 9/1979 | Boyer | 435/32 |
| 4,225,669 | 9/1980 | Melnick et al. | 435/32 |
| 4,343,782 | 8/1982 | Shapiro | 424/3 |
| 4,423,145 | 12/1983 | Stampner et al. | 435/32 |
| 4,424,201 | 1/1984 | Valinsky et al. | 424/3 |

OTHER PUBLICATIONS

Fox, I. J., et al., *Proc. Mayo Clinic* 32:478–484 (1957).
Schad, H., et al., *Pfluegers Arch. Eur. J. Physiol.* 370(2):139–144 (1977).
Wanda, P. E. and Smith, J. D., *J. Histochem. Cytochem.* 30:1297–1300 (1982).
Axelrod, D., *Biophysical J.*, 26:557–574 (1979).
Honig, M. G. and Hume, R. I., *J. Cell Biology*, 103:171–187 (1986).
Johansson, L. B. A., et al., *J. Chem. Soc., Faraday Trans.* 1:81(6): 1389–1400 (1985).

*Primary Examiner*—Sam Rosen
*Assistant Examiner*—D. A. Saunders
*Attorney, Agent, or Firm*—Stuart R. Suter; Alan D. Lourie

[57] ABSTRACT

Methods for determining growth rate of cells growing in vivo and in vitro. Cells are labelled with cyanine dyes and changes in plasma membrane cyanine dye levels are used to determine growth rate. Cell growth rate determinations are utilized to monitor transplanted bone marrow cell engraftment and post-surgical corneal epitheal cell growth. The invented methods also are used to determine tumor cell sensitivity to cancer therapeutic agents, yeast sensitivity to antifungal agents, and bacteria sensitivity to antibacterial agents.

19 Claims, 4 Drawing Sheets

CELL GROWTH RATE DETERMINATION BY MEASUREMENT OF CHANGES IN CYANINE DYE LEVELS IN PLASMA MEMBRANES

BACKGROUND OF THE INVENTION

1. Field of the Invention

This invention relates to novel methods for measuring cell growth rate in vivo and in vitro.

2. Background Information

Currently, there are two popular methods for measuring cell growth. One method is to count the number of cells at the beginning of an analysis period, and then count the number of cells at the cell of that period to measure the increase in cell number. Cell counting can be achieved by using microscopic methods with a hemocytometer or by instrument aided methods using a Coulter Counter or other flow cytometer. another Methodology for measuring cell growth is to determine the uptake of tritiated thymidine using beta counting methods. In this methodology, the cell number is determined at the initiation of the experiment and then tritiated thymidine is placed in with the cells. At periodic intervals, aliquots of the culture are removed, counted, and washed free of unbound tritiated thymidine. These washed aliquots are then subjected to Trichloroacetic Acid (TCA) precipitation followed by scintillation counting of the radioactively labelled solid precipitate to measure tritiated thymidine incorporation into DNA. This methodology merely measures the rate of DNA synthesis and does not measure the cell growth per se. Because of the relative ease of this methodology, however, it generally is the methodology of choice when looking at cell stimulation. Another method used to determine cell proliferation activity is to look at the number of mitoses per hundred cells in any tissue under examination. This methodology is not extremely accurate because the preparation procedure causes loss of cells. In general, these assays work well in vitro but are difficult to apply to measurements of cell growth in vivo.

Growth rate of tissues can be estimated by removing the tissue and monitoring in vitro pulse incorporation of tritiated thymidine. The tissue is sectioned into 30 micron sections and exposed to tritiated thymidine for thirty (30) minutes. The unincorporated tritiated thymidine is washed away and a nuclear emulsion is placed over the section where radioisotope disintegrations expose the film. The emulsion is developed and fixed; the tissue is stained with Hematoxylin and Eosin stain; then the section is examined microscopically to determine labelled fraction. This technique is labor intensive and time consuming.

Cyanine dyes have been used in various biological applications. Dioxacarbocyanine dyes have been used in performing white blood cell differential counts. Gunter Valet, Max Planck Ges Wissensch; Patent Accession Number 84-102307/17, *Simultaneous Quantitative Determination of Blood Cells by Selective Staining and Measuring Volume and Fluorescence*. The dyes utilized in these studies, however, are short chain carbocyanine dyes (less than ten carbons) and respond to changes in membrane potentials. Furthermore, the short chain carbocyanine dyes enter the cell's mitochondria, are cytotoxic, and, when the cells are washed, these dyes easily leak out of the cell whether or not the membrane potential of the cell is changed. Other short aliphatic chain cyanine dyes are used in many other biological assays. The short chain molecules, however, respond to membrane potentials and cross the cell membrane, penetrating into the mitochondria. H. M. Shapiro, U.S. Pat. No. 4,343,782, Aug. 10, 1982. The short chain dyes also are toxic to cells and cannot be used to determine cell growth rate.

Tricarbocyanine dyes (Fox, I. J., et al., Proc. *May Clinic*, 32: 478–484, 1957) and Evans-Blue dye (Schad, H., et al., *Pfluegers Arch. Eur. J. Physiol.*, 370(2): 139–144, 1977) have been used in vivo to estimate cardiac output by a dilution method. Dow (Dow, P., *Physiol. Rev.*, 36: 77–102, 1956) describes the method as injection of a known amount of some intravascular indicator on the venus side of the lungs, and measurement of the time course of arterial concentration of the indicator to determine the volume between the points of injection and sampling. These dyes are not used to stain cells.

SUMMARY OF THE INVENTION

Presently invented are novel methods for measuring cell growth rate. According to the present invention, viable cells first are labelled with cyanine dyes. Cell growth rate is determined by measuring changes in the levels of cyanine dye in the plasma membranes of daughter cells derived from cyanine dye-labelled parent cells. The invented methods for measuring growth are used, for example, in vivo to monitor healing of corneal epithelia, and engraftment of transplanted bone marrow cells. In vitro uses of the invented methods include determining sensitivity of tumor cells to various chemotherapeutic agents.

DETAILED DESCRIPTION OF THE INVENTION

Figure 1:
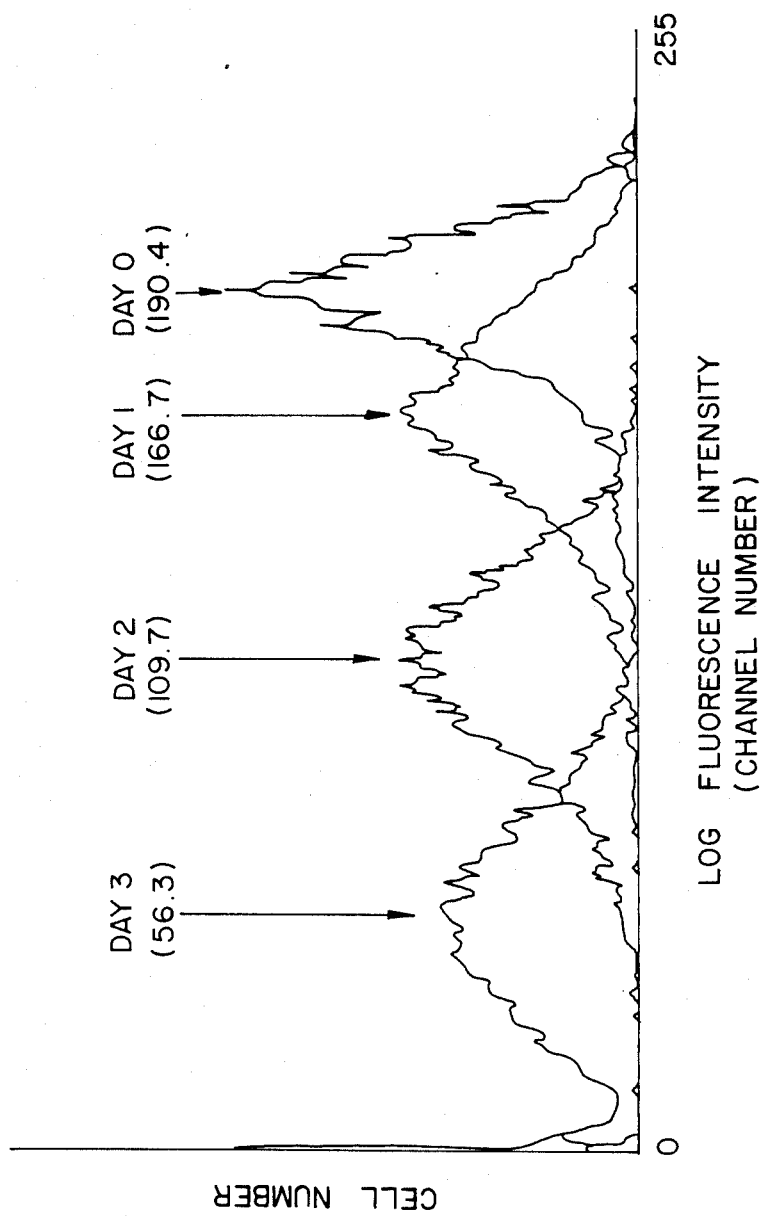
FIG. 1 is a graph showing cellular fluorescence intensity decreases as a function of time.

In the invented methods for determining cell growth rate, the cells are labelled with cyanine dyes. Compounds having the following structure are referred to herein as cyanine dyes:

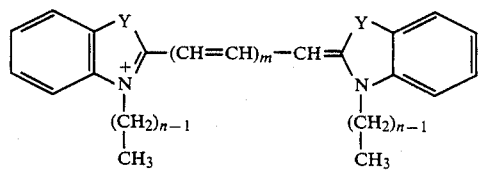

in which:
  Y is oxygen, sulfur, methylene or alkyl-substituted methylene;
  m is 0–3; and
  n is 12–22. As used herein, alkyl-substituted methylene refers to mono- or di-substituted methylene having any combination of methyl, ethyl, or propyl substituents.

Compounds of the above structure are referred to by the following generally understood shorthand formula:

DiYC$_n$(2m+1)

Sims, P. J., et al., *Biochem*, 13: 3315 (1974). Thus, for example, the compound wherein Y is sulfur and having three carbons bridging the rings and two fourteen carbon aliphatic chains is referred to as DiSC$_{14}$(3). Similarly, DiIC$_{14}$(5) indicates the compound wherein Y is isopropyl, and having five carbons bridging the rings and two fourteen carbon aliphatic chains.

Included within compounds referred to herein as cyanine dyes are compounds of the above structure having one or more substitutions provided such substituted compounds are soluble in a cell labelling media for at least as long as needed for labelling and have a sufficiently high membrane partition coefficient to remain associated with labelled cell membranes. Such compounds also must not significantly affect cell viability in the concentrations required for labelling. Solubility in cell labelling media is determined as shown below by dispursing a cyanine dye in the labelling media and, by standard spectrofluorometric techniques, measuring fluorescence intensity over time. Decreasing fluorescence intensity indicates dye precipitation and adherence to vessel walls. Whether the dyes remain associated with cell membranes is determined, for example, using known flow cytometric procedures to monitor fluorescence intensity of red blood cells reinjected into the donor animal after labelling. Essentially constant fluorescence intensities of the labelled cells after reinjection establishes stability of the dye in cell membranes.

Cyanine dyes used in the present invention can be purchased from various sources such as Molecular Probes, Inc., Eugene, Oreg., and can be prepared from available starting materials using known synthetic methods. Hamer, F. M., *The Cyanine Dyes and Related Compounds*, Interscience Publishers (1964).

Using the described procedures any viable cell can be labelled with cyanine dyes. As used herein, the term cell includes nucleated cells such as white blood cells, various tumor cells, other mammalian cells (for example, tissue culture cells) yeast, and bacteria. A cell is viable if it is able to grow or function essentially as expected for cells of its type.

Cell labelling is performed in a medium that is nonlethal to cells and that provides for reproducible cell labelling. To give the medium the necessary characteristics, osmolarity regulating agents in which cyanine dyes form stable solutions for at least as long as required for labelling are used. Acceptable osmolarity regulating agents include agents such as sugars, for example monosaccharides such as glucose, fructose, sorbose, xylose, ribose, and disaccharides such as sucrose, sugar-alchols, such as mannitol, glycerol, inositol, xylitol, and adonitol, amino acids such as glycine and arginine, and certain Good's buffers such as N-tris(hydroxymethyl)-methyl-3-aminopropanesulfonic acid and those listed in Table II, below. Good, N. E., et al., *Biochem.* 15, 467–477 (1966), Good, N. E. and S. Izawa, *Methods Enzymol.*, 24, Part B, 53 (1968), Feguson, W. J., et al., *Anal. Biochem.* 104: 301–310 (1980). Some cell lines, however, may be sensitive to one or more of the osmolarity regulating agents, especially sugar-alcohols. Thus, prior to labelling, standard tests are conducted to make certain that the cells are viable in the intended osmolarity regulating agent. Additionally, small amounts of buffering agents may be added to the labelling medium to regulate hydrogen ion concentration.

The effect on cell viability of exposure to a variety of osmolarity regulating agents was determined by measuring the doubling time of Yac cells after the cells were exposed for thirty minutes to a variety of osmolarity regulating agents. Yac cells are a mouse lymphoma tissue culture cell line publically available from the American Type Culture Collection and is described by Kiessling, R., *European J. Immunology* 5: 112–117 (1975). As the data shown in Table 1 demonstrate, when compared to phosphate buffered saline, exposure to sucrose, glucose, and the Good's buffers: TAPS, CAPS, EPPS, HEPPSO, and DIPSO resulted in negligible effects on cell doubling time which indicates the absence of exposure-related cellular toxicity.

TABLE 1

| Osmolarity Regulating Agent | Doubling |
|---|---|
| Phosphate Buffered Saline | 31.0 |
| Sucrose | 41.0 |
| Glucose | 34.5 |
| TAPS | 32.7 |
| CAPS | 45.8 |
| EPPS | 32.2 |
| HEPPSO | 23.4 |
| DIPSO | 36.7 |
| 3-Amino-1-propanesulfonic acid | 99.6 |
| Sodium 3-(N—morpholino)propanesulfonic acid (MOPS) | A |
| 2-Amino-2-methyl-1,3-propanediol | B |
| 2-Amino-2-methyl-1-propanol | B |
| N—tris(hydroxymethyl)methylaminoethane-sulfonic acid (TES) | B |
| N,N—bis(2-hydroxyethyl)-2-aminoethane-sulfonic acid (BES) | A |
| 3-(Cyclohexylamino)-2-hydroxy-1-propane-sulfonic acid (CAPSO) | A |
| Triethanolamine | B |
| Tris(hydroxymethyl)aminoethane (TRIZMA) | B |
| Bis-tris propane | B |
| 2-(N-morpholino)ethanesulfonic acid (MES) | B |
| 3-[Dimethyl(hydroxymethyl)methylamino]-2-hydroxypropanesulfonic acid (AMPSO) | A |
| N,N-bis(2-hydroxyethyl)glycine (BICINE) | 57.7 |
| 3-[(-3-Cholamidopropyl)dimethylammonio]-1-propanesulfonate (CHAPS) | B |
| 3-[N-tris(hydroxymethyl)methylamino]-2-hydroxypropanesulfonic acid (TAPSO) | 63.6 |
| 3-(N-morpholino)-2-hydroxypropane-sulfonic acid (MOPSO) | 178.4 |
| 2-[(2-Amino-2-oxoethyl)amino]ethane sulfonic acid (ACES) | 1038.4 |
| Bis(2-hydroxyethyl)imino-tris-(hydroxymethyl)methane (BIS-TRIS) | A |
| 2-(N-cyclohexylamino)ethane sulfonic acid (CHES) | 51.5 |
| N-tris-(hydroxymethyl)methylglycine (TRICINE) | A |
| Glucosamine | 288.4 |
| Imidazole | B |
| Glycylglycine | 66.9 |

A - No growth or partially cytotoxic
B - Acutely cytotoxic

Table II shows various osmolarity regulating agents that were examined for cyanine dye solubility. All measurements of concentration were made after removal of precipitates by centrifugation and dissolving small aliquots of osmolarity regulating agents containing cyanine dyes into ethanol for spectrofluorometric analysis.

The dyes used were DiSC$_{14}$(5) and DiOC$_{14}$(3), and the osmolarity regulating agents were at iso-osmotic concentrations for mammalian cells. Reductions in fluorescence intensity from the ethanol solution standard directly correlate with reductions in cyanine dye solubility.

TABLE II

| Osmolarity Regulating Agent | Relative Fluorescence Intensity (CONC) | |
|---|---|---|
| | DiSC$_{14}$(5) | DiOC$_{14}$(3) |
| Ethanol | 100 | 100 |
| Glucose | 31 | 100 |
| Fructose | 35 | 100 |
| Sorbose | 40 | 100 |
| Sucrose | 41 | 100 |
| Xylose | 36 | 19–52 |
| Ribose | 24 | 100 |
| Lyxose | 0.12 | 1.8 |
| Glycine | 31 | 93 |
| Arginine | 17 | 17.2 |
| Glycerol | 39 | 99.5 |
| Inositol | 42 | 92 |
| Xylitol | 34 | 76.4 |
| Mannitol | 29 | * |
| Adonitol | 34 | ND |
| Tris(hydoxymethyl)-methylaminopropane sulfonic acid (TAPS) | 18 | ND |
| 3-(Cyclohexylamino)-1-propanesulfonic acid (CAPS) | 40 | ND |
| N-(2-Hydroxyethyl)piperazine-N-3-propanesulfonic acid (EPPS) | 18 | ND |
| N-2-hydroxyethylpiperazine-N-2-hydroxypropane-sulfonic acid (HEPPSO) | 20 | ND |
| 3-[N-N-bis(2-hydroxyethyl)-amino]-2-hydroxypropane-sulfonic acid (DIPSO) | 43*** | ND |
| NaCl | 6 | 1.7 |
| Phosphate Buffered Saline | 2.1 | 6.5 |
| Na$_2$SO$_4$ | 7.4 | 1.6 |
| NaI | 1.1 | 0.14 |
| Choline Chloride | 11** | 6.3 |
| Choline Iodide | 0.16 | 2.3 |

*Precipitate in ethanol, no data obtainable.
**Artifact due to large crystals that did not pellet.
*** Precipitate in ethanol (data questionable).
ND Not Determined As can be seen from Table II, cyanine dyes are much less soluble in the presence of classical salts than in the presence of sugars, except lyxose, sugar-alcohols, amino acids, and the Good's buffers, TAPS, HEPPSO, DIPSO, CAPS, and EPPS. Additionally, stability of DiSC$_{14}$(5) solutions in sugars such as glucose, fructose, ribose, sorbose, sucrose, and xylose, sugar-alcohols such as glycerol, inositol, xylitol, and adonitol, and amino acids such as glycine and arginine was determined. The cyanine dye was stable in the tested solutions for at least twenty minutes, which is sufficient time for reproducible labelling, and in many of the agents the amount of cyanine dye in solution had not significantly decreased at sixty minutes.

Further, the solubility of cyanine dyes in a medium containing classical salts and osmolarity regulators in which the dyes are soluble was evaluated. The solubility of DiSC$_{14}$(5) in iso-osmotic glucose solution was not significantly affected by dilution with distilled water. DiSC$_{14}$(5) solubility in iso-osmotic glucose solution, however, was reduced significantly by dilution with only approximately 20% iso-osmotic sodium chloride solution. Thus, reproducible cell labelling with cyanine dyes can be performed in media containing no more than small amounts of classical salts, such as sodium chloride, potassium chloride, calcium chloride, sodium acetate, potassium acetate, sodium sulfate, sodium iodide, choline chloride, or choline iodide, and preferably is performed in a medium in which no classical salts are used to regulate osmolarity.

Cells cyanine dye labelled using the presently invented procedure were analyzed to determine the effect of labelling on cell viability. V79 cells which are available from the American Type Culture Collection, Rockville, Md., and are described in Prescott, D. M., Ann. New York Acad. Sci., 397: 101–109 (1982), were labelled with a solution containing DiOC$_{14}$(3) at a concentration of $10^{-5}$ or $4 \times 10^{-5}$M and the growth kinetics of the stained cells were compared to unstained cells and an equal mixture of stained and unstained cells. Cell doubling time was unaffected by cyanine dye labelling. Thus, labelling had no effect on cell growth. Also, several other standard tests of cell viability such as Trypan Blue Exclusion and Propidium Iodide exclusion confirmed an absence of effect on cell viability of cyanine dye labelling according to the described procedures.

To test in vivo stability of cells cyanine dye labelled according to the presently invented method, rabbit red cells were withdrawn, labelled with DiSC$_{14}$(5), and reinfused. Periodically thereafter, blood samples were obtained and analyzed for percent labelled cells and fluorescence intensity of the labelled cells. The number of circulating red cells decreased linearly as a function of time and the measured 52 day lifetime of labelled cells correlated closely with the 40 to 60 day average reported lifetime of rabbit red cells. Thus, cyanine dye labelling did not affect the clearance rate of red blood cells.

In all but one of the five rabbits tested, fluorescence intensity of the stained cells remained essentially unchanged 60 days after labelling and reinjection. In the fifth animal, not more than 20% of the cyanine dye had migrated from the labelled cells after 60 days in the rabbits circulation. These data combined with data from tissue culture showing no transfer of dye from labelled to unlabelled cells demonstrates that the cells are stably labelled with the dyes.

Cyanine dye-labelled viable cells are used in the invented methods for determining cell growth rate. Growth rate is determined by measuring changes in the levels of cyanine dye in the plasma membranes of the cells. Each time a cell divides the plasma membrane associated cyanine dye is distributed equally between the daughter cells. Thus, serial measurements of the plasma membrane cyanine dye levels of labelled, growing cells are used to calculate growth rate.

Flow cytometric methods using standard techniques are preferred for measuring plasma membrane cyanine dye levels of non-adherent cells or cells that can be removed from their growth substrate and suspended as single cells. An adherent cell cytometer (Meridian ACAS 470) is preferred for cases where removal from the growth substrate is difficult or not feasible.

Determinations of cell growth rate are used in a variety of applications. For example, growth rate of tissue culture cells is measured to optimize growth conditions. Sensitivity of tumor cells to chemotherapeutic agents is determined by measuring cell growth rate in media containing these agents. Similarly, sensitivity of yeast cells to various antifungal agents is determined by measuring the growth rate of the yeast cells in media containing antifungal agents.

The invented methodology also is used to monitor growth rate of tissue cells in vivo. For example, bone marrow transplant engraftment is determined by measuring bone marrow cell growth rate following transplant. Growth rate of other in vivo cells, such as corneal epithelial cells, is measured to determine post-traumatic or post-surgical healing.

The following examples illustrate the present invention and do not limit the scope of the invention defined above and claimed below.

EXAMPLE 1

Method for Staining Tissue Culture Cells

I. Preparation of Cells

Log phase tissue culture cells are used to obtain best results. Suspension cultures are removed from the culture vessel and placed into polypropylene centrifuge tubes.

When using monolayer cultures, supernatants must be removed and the adherent cells washed with calcium and magnesium free phosphate buffered saline solution to remove serum proteins from the flask. Trypsin-EDTA solution (Gibco Laboratories, Grand Island, N.Y., #610-5300) is added to cover the bottom of the flask and is allowed to incubate at room temperature until the cell monolayer is dislodged and disaggregated. The resultant cell suspension is transferred to a polypropylene centrifuge tube and an equal volume of culture media containing 10% Fetal Bovine Serum (FBS) (Hazelton) is added to arrest the enzymatic action of the trypsin.

Cells are centrifuged at 400xg for ten minutes at room temperature. Supernatants are aspirated and an equal volume of iso-osmotic mannitol is replaced for resuspension of the cell pellet. This mannitol wash is to remove the plasma proteins from the cell suspension and prepare cells for staining. Cells are once again centrifuged at 400xg for ten minutes at room temperature. The supernatants are aspirated and the resultant cell pellet is resuspended in mannitol solution at a concentration of $2 \times 10^6$ cells/ml for staining. Some cell lines, however, are sensitive to the use of a sugar alcohol (mannitol); in such cases an iso-osmotic glucose solution (MW 180.16, 54.05 g/l) may be used.

II. Preparation of Stock Dye Solutions $2 \times 10^{-3}$M stock solutions are prepared as follows in absolute ethanol.

| | |
|---|---|
| DiO—$C_{14}$(3) | MW 800 (1.600 mg/ml) |
| DiS—$C_{14}$(5) | MW 814 (1.628 mg/ml) |
| DiO—$C_{18}$(3) | MW 936 (1.872 mg/ml) |
| DiI—$C_{14}$(5) | MW 850 (1.700 mg/ml) |

All dyes are obtained from Molecular Probes, Eugene, Oreg.

Dye stocks are sonicated to insure complete solubility of the dye and to minimize adherence to the tubes. Polystyrene tubes are used for preparation of stock solutions so that solubility of the dye can be observed. Polypropylene tubes, however, are used to stain cells because cyanine dyes in an aqueous environment are much less adherent to polypropylene when compared to polystyrene.

III. Cell Staining

Cells are adjusted to a concentration of $2 \times 10^6$ cells/ml in iso-osmotic mannitol. To stain cells, $2 \times 10^{-3}$M stock dye solution is added to the staining solutions at 5 $\mu$l of dye per 1 ml of cell suspension giving a final concentration of 10 $\mu$M. The sample for staining is pipetted or vortexed to thoroughly mix the sample. Cells are incubated with the dye for ten minutes, after which a small aliquot is removed for examination under a fluorescent microscope to insure that intense and uniform staining has occurred. The DiO dye series uses microscope filters selective for 488 nm excitation light, while the DiS and DiI dye series requires excitation near 575 nm for observation of fluorescence.

After the incubation period, an equal volume of PBS is added to the stain-cell suspension. The cells are centrifuged at 400xg for ten minutes at 20° C. The supernatant is aspirated and the pellet is resuspended in PBS. The centrifugation procedure is repeated and the resultant supernatant is observed for the presence of dye. If dye is apparent in the supernatant, washing is repeated until the supernatants are devoid of free dye as measured by spectofluorometry. After the final wash, the supernatant is removed and the pellet resuspended to the desired concentration in a suitable culture medium. All procedures are performed under sterile conditions.

EXAMPLE 2

Measuring Growth Rate of Tissue Culture Cells

V79 cells were stained with $DiOC_{14}(3)$ as described in Example 1. Fluoresence intensity was measured using an EPICS 750 Flow Cytometer (Coulter Electronics, Inc.). Immediately after staining, fluorescence intensity of an aliquot of the stained cells was measured. The remaining cells were grown in a humidified air-$CO_2$ (7.5% $CO_2$) incubator at 37° C. in a standard complete growth medium. On days one, two, and three after staining, aliquots of cells were removed for fluorescence intensity determinations.

FIG. 1 shows the log fluorescence intensity profile of the growting V79 cells. The numerical value above each peak is the mean log fluorescence intensity on each day. As FIG. 1 shows, the mean log fluorescence intensity diminishes daily as the cells grow in culture.

From fluorescence measurements, growth rate is determined from the slope of the regression line fit to the linear portion of a plot of log fluorescence intensity versus time.

Figure 2:
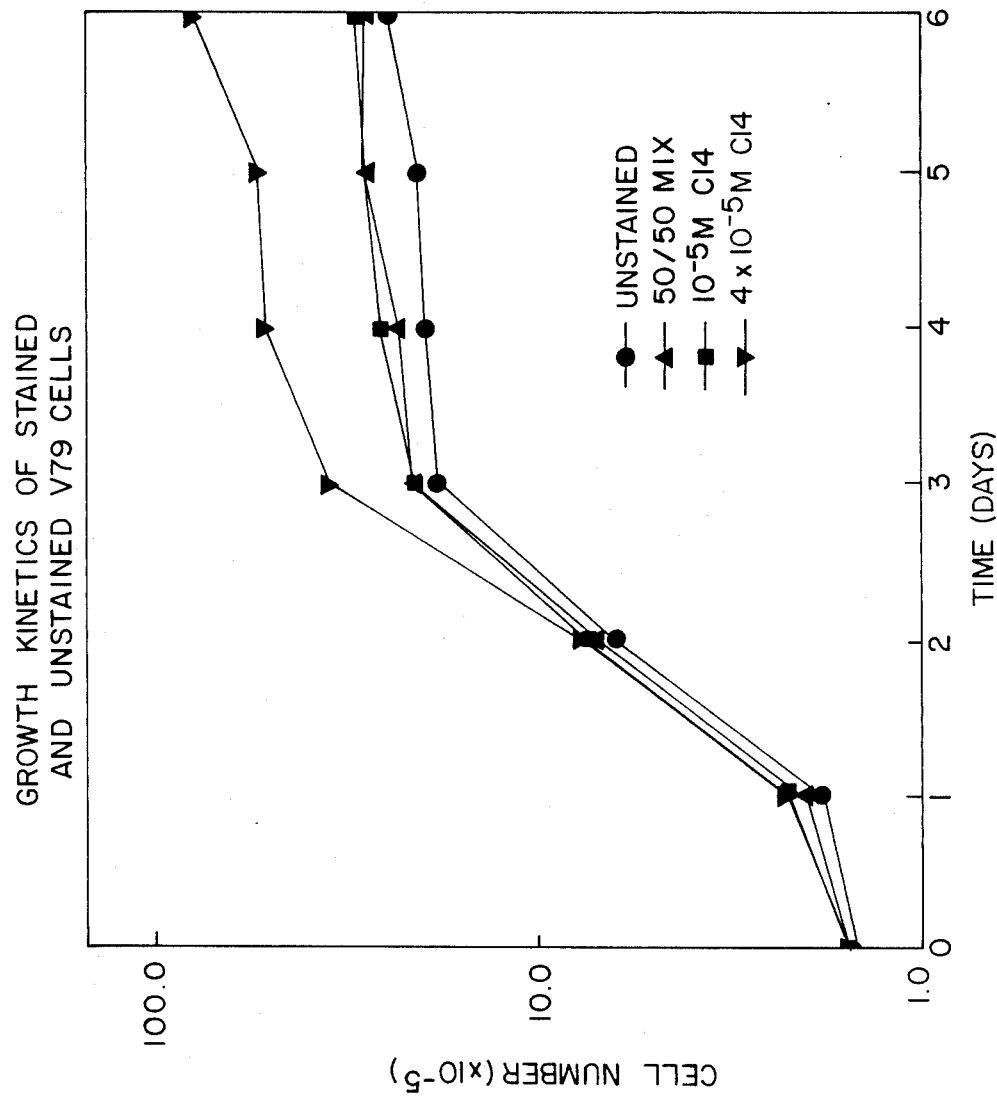
FIG. 2 is a graph showing growth curves of stained and unstained cells.

To make certain that staining the cells did not affect growth rate, growth rates of stained and unstained V79 cells were compared. The results shown in FIG. 2 demonstrate that unstained cells grew at a rate equivalent to cells stained with $10^{-5}$M dye or $4 \times 10^{-5}$M dye, or an equal mixture of stained and unstained cells.

Since dye transfer from stained to unstained cells would result in erroneous growth rate determinations, stained and unstained cells were grown together in culture. A human colon carcinoma cell line, HT29, which is available from the American Type Culture Collection, Rockville, Md., and is described in J. Fogh and G. Tremp, *Human Tumor Cells In Vitro*, pp. 115-159, Plenum Press, New York (1975), stained with $DiOC_{14}(3)$ and unstained human promyelocytic leukemia, HL60, cells, available from the American Type Culture Collection, Rockville, Md., and described in Collins, S. J., et al., *Nature*, 270: 347-349 (1977), were grown together in a ratio of 1:1 stained to unstained cells. These data are displayed in FIG. 3.

Figure 3:
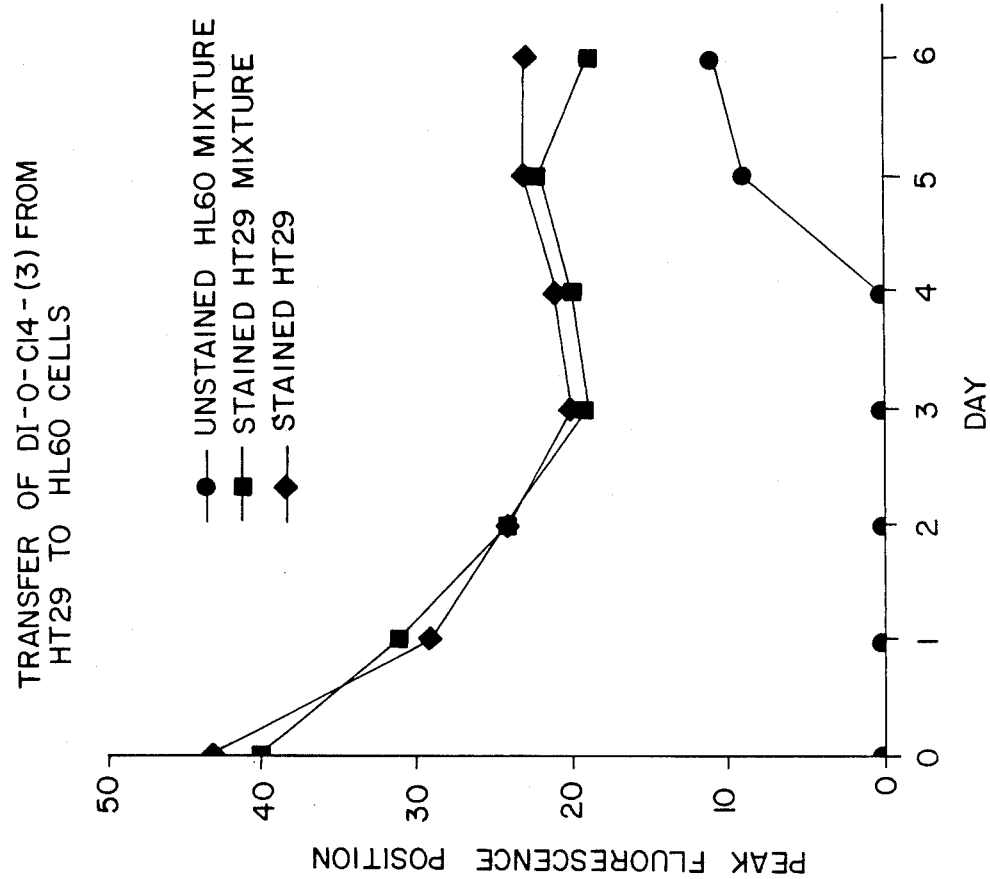
FIG. 3 is a graph showing lack of dye transfer from stained to unstained cells.

In FIG. 3, the fluorescence intensity of the stained HT29 cells cultured alone (diamonds) demonstrated the characteristic reduction in fluorescence intensity as a function of time in culture. The unstained HL60 cells had very little fluorescence for four (4) days, after which there appeared some modest increase in fluorescence intensity. Furthermore, the stained HT29 cells which were co-cultured with HL60 cells (squares) lost fluorescence intensity exactly as the unmixed HT29 cells until approximately day five, where there appeared some additional but minimal loss of fluorescence intensity. From these data it is clear that perhaps the HL60 cells are picking up some fluorescence after being in culture for four (4) days with the HT29 cells. It should be noted that the HL60 cells, however, are promyelocytic and have some capability to phagocitize cells and debris. The increase in fluorescence intensity experienced after day 4 in the unstained subpopulation of the mixed culture may in fact be a result of phagocytosis of fluorescent debris. More importantly, for four days in culture, there was no increase in fluorescence intensity of the unstained HL60 cells. Furthermore, the stained HT29 cells in the same mixture appear to have the same fluorescence kinetics as the HT29 cells which are unmixed. Thus, cell-to-cell dye transfer does not lead to incorrect growth rate determinations.

EXAMPLE 3

Measuring Growth Rate of Tumor Cells

If the tumor cells being studied are a tissue culture line adapted to in vitro culture conditions, then the cells are stained and evaluated as outlined in Examples 1 and 2. If the tumor cells being studied are from tumor tissue explants then they are dissaggregated into single cells by standard techniques and plated onto Lab-Tech tissue culture chamber slides. The cells are stained using the cyanine dyes as outlined in Example 1. They are then placed into an humidified air-$CO_2$ incubator at 37° C. and allowed to equilibrate. At periodic intervals the slides are placed onto the microscope stage of an adherent cell cytometer (i.e., Meridian ACAS 470) and measurements of fluorescence intensity are made. The locations of the cells relative to an index mark are determined by the computer so that serial measurements of fluorescence intensity can be made. The slide is returned to the incubator to allow the cells to continue growing. The microscope slide should contain a fluorescence standard such as Coulter fullbright polystyrene microspheres (Coulter Electronics, Hialeah, Fla. that do not change fluorescence intensity with time in culture. This standard is used to make comparison measurements of fluorescence intensity.

Tumor cells are identified from normal stromal cells on the basis of morphometric parameters using phase optics on the microscope or fluorescent monoclonal antibodies specific to tumor cells. The measurement of cell growth is made by monitoring dilution of the cyanine fluorescence in the tumor cells as each cell divides and applying the equations of Example 9.

The measurement of fluorescence intensity can also be made using a flow cytometer. The cells, however, are removed from the microscope slide before flow cytometric analysis is made. This procedure does not permit the serial quantification of dye dilution on the same cells day after day. In some instances, however, such as leukemia cells, this approach is preferred.

The process of measuring in vitro cell growth is accomplished on cells that have been cultured in optimal growth medium or in the presence of various levels of agents used to treat tumors. The ability of the therapeutic agent to inhibit the tumor cell growth as measured by inhibition of fluorescence intensity reduction, is a measure of the effectiveness of that agent to kill tumor cells.

EXAMPLE 4

Measuring White Blood Cell Growth Rate

Lymphocytes are removed by venipuncture or splenic dissection using standard techniques. The cells are labelled with a cyanine dye using the protocol listed in Example 1 but substituting glucose or sucrose for mannitol as the osmotic support medium. The stained cells then are aliquoted into microtiter dishes at a level of $5 \times 10^5$ cells per well (Mazumder, A., Grimm, E. A., Zhang, H. Z., and Rosenberg, S. A., *Cancer Res.* 42, 918 (1982)) and incubated with the appropriate mitogen such as Interleukin-2, sodium periodate ($IO_4$-), phytohemagglutinin, concanavalin A, pokeweed-mitogen and B Cell Growth Factor (BCGF). The cells are placed into a 37° C. humidified air-$CO_2$ incubator and allowed to grow. At periodic intervals cells are removed from the culture vessel and examined by flow cytometric procedures. The data obtained are similar to that obtained by the process of Example 2 and are analyzed using the equations of Example 9.

EXAMPLE 5

Measuring Bacteria Growth Rate

The cells are labelled with a cyanine dye using the protocol listed in Example 1 but substituting glucose or sucrose for mannitol as the osmotic support medium. The stained cells then are aliquoted into microtiter dishes at a level of $5 \times 10^5$ cells per well in a nutrient broth. The cells are placed into a 37° C. humidified incubator and allowed to grow. At periodic intervals cells are removed from the culture vessel and examined by flow cytometric procedures. The data obtained are similar to that obtained in the process of Example 2 and are analyzed using the equations of Example 9.

The process of measuring in vitro cell growth is accomplished on cells that have been cultured in optimal growth medium or in the presence of various levels of antibiotics which are being tested as antibacterial agents. The ability of the bactericidal agent to inhibit the bacterial cell growth as measured by inibition of cellular fluorescence intensity reduction, is a measure of the effectiveness of that agent to kill bacteria.

EXAMPLE 6

Measuring Yeast Growth Rate

The cells are labelled with the cyanine dye using the protocol listed in Example 1 but substituting glucose or sucrose for mannitol as the osmotic support medium. The stained cells then are aliquoted into microtiter dishes at a level of $5 \times 10^5$ cells per well in a nutrient broth. The cells are placed into an incubator and allowed to grow. At periodic intervals cells are removed from the culture vessel and examined by flow cytometric procedures or by adherent cell cytometric procedures (Meridian ACAS 470). The data obtained are similar to that obtained by the process of Example 2 and are analyzed using the equations of Example 9.

The process of measuring in vitro cell growth is accomplished on cells that have been cultured in optimal growth medium or in the presence of selected levels of compounds which are being tested as antifungal agents. The ability of the fungicidal agent to inhibit the fungal cell growth as measured by inibition of cellular fluorescence intensity reduction, is a measure of the effectiveness of that agent to kill fungi.

EXAMPLE 7

Measuring Growth Rate of Bone Marrow Cells

Bone marrow cells are removed by aspiration (Illinois needle) or by core biopsy (Jamshiti needle) from the sternum or iliac crest. The cells are labelled with a cyanine dye using the protocol listed in Example 1 but substituting glucose or sucrose for mannitol as the osmotic support medium. The cells are subjected to flow cytometric analysis to determine the level of fluroescence intensity prior to infusion of the bone marrow cells into the recipient. Labelled cells are injected intravenously and an appropriate time interval is allowed to elapse before a sample of peripheral blood and bone marrow is taken. Blood and marrow are taken from the recipient, mixed with anticoagulants, and prepared according to standard techniques for flow cytometric analysis. These samples contain cells which are growing and cells which are in cell cycle arrest. The histograms will be complex but are analyzed for cell growth similar to the data obtained in the process of Example 2 by applying the equations of Example 9.

Because the tracking dyes are fluorescence green, another dye coupled to monoclonal antibodies is used to identify cells from each of the cell lineages found in marrow. Using a monoclonal antibody which stains red cells and their precursors, the red fluorescence is used to identify this lineage and then monitor the reduction in green fluorescence (and therefore cell growth) of the cells in the red cell lineage.

Similar two color approaches are used to evaluate lymphoid, myeloid, and monocyte cell growth.

EXAMPLE 8

Measuring Corneal Epitheal Growth Rate

This methodology is used to monitor growth of corneal epithelial cells after transplant and uses technology that is not injurious to cell growth or painful to the eye when monitoring cell growth. Immediately after transplant, the eye is bathed in an opthalmic formulation of the cyanine dye which absorbs light at wavelengths greater than 680 nm. The procedure also is carried out using dye which absorbed light at wavelengths lower than 680 nm, however, the excitation beam causes severe headaches when the tissue is examined.

At time zero, infrared photographs are taken (wavelengths greater than the absorbance maximum of dye) while exciting the cyanine dye bound to the cornea. The fluorescence intensity level is a measure of cell staining at time zero. At subsequent times the eye is photographed and the image is compared to the time zero photograph. In areas where there is cell growth, the fluorescence intensity of the cells decreases. Quantitative assessment of the fluorescence intensity is used to determine the number of cell doublings.

EXAMPLE 9

Calculating Cell Growth Rate

The following mathematical formula is used to calculate cell doubling time:

$$T_D = \frac{0.693(t_2 - t_1)}{\ln F(t_1) - \ln F(t_2)}$$

wherein:
$T_D$ is the cell doubling time,
$t_2$ and $t_1$ are any times during log phase cell growth, and
$F(t_2)$ and $F(t_1)$ are the mean cellular fluorescence intensity at times $t_2$ and $t_1$, respectively,
ln signifies the natural (base e) logarithm.

The number of cell doublings occuring during a period of growth is determined by the formula:

$$N = \frac{\ln F_o - \ln F(t)}{\ln 2}$$

wherein:
N is the number of cell doublings,
$F_o$ is the initial fluorescence intensity, and $F(t)$ is the fluorescence intensity at any time after a period of cell growth. For determination of the number of cell doublings, the fluorescence measurements do not have to be made during the log phase of cell growth.

The following derivation demonstrates that the above formulae accurately determine cell doubling time and the number of cell doublings, and that the behavior of plasma membrane cyanine dye levels in growing cells predicted by mathematical modeling parallels that actually measured.

The derivation is based on the following assumptions:

1. Cells are set in culture at low density with an initial cell number ($N_o$), and average initial fluorescence intensity ($F_o$) and a cell cycle time ($T_2$).
2. Dye distributes evenly to daughter cells on cell division.
3. There is no lag time in the culture.
4. Cell death is negligible.
5. Staining is permanent; there is no cell-cell dye transfer.

Based on the second assumption above, the average population fluorescence should be inversely proportional to the number of cells in the population at any time t. This relationship is defined in equation 1, $$F(t)N(t) = K \tag{1}$$

where $F(t)$ and $N(t)$ are the average population fluorescence and cell number at time t, respectively. K is a proportionality constant, to be defined. If we evaluate this equation at time zero, then it follows that $K = F_o N_o$. Substituting this into equation 1 and solving for $F(t)$ gives, $$F(t) = F_o N_o (1/N(t)). \tag{2}$$

$F_o$ and $N_o$ were defined in assumption 1.

It is obvious from equation 2 that the fluorescence kinetics must be directly related to the growth kinetics, if the dye being used acts in an ideal fashion. The form of the relationship defining the fluorescence kinetics will now be determined. The cell number in equation 2 follows common growth kinetics defined below, $$dN(t)/dt = AN(t) \tag{3}$$

where A is the proportionality constant relating the rate of population growth to the number of cells in the population. Equations 4 to 7 show the simple solution of equation 3.

$$dN(t)/N(t) = d \ln N(t) = A dt \qquad (4)$$

$$N(t) = \exp(At + C) \qquad (5)$$

$$N(t) = N_o \exp(At) \qquad (6)$$

$$N(t) = N_o \exp(0.693 t/T_2) \qquad (7)$$

The result in equation 7 can be substituted into equation 2 to solve for F(t).

$$F(t) = \frac{F_o N_o}{N_o \exp(0.693 t/T_2)} \qquad (8)$$

This reduces directly to, $$F(t) = F_o \exp(-0.693 t/T_2). \qquad (9)$$

The interpretation of this equation requires careful consideration. First, because we have assumed negligible cell death, $T_2$ represents the cell cycle time, not the cell doubling time. This point will be considered more carefully below. If there is cell death, this equation is still valid, as long as the dye bound to dead cells is not reabsorbed by the live cells. The case where reabsorption occurs will be treated below. In the case where a fraction of the population is not growing, equation 9 is valid only for the growing fraction. Consequently, $F_o$ and $N_o$ apply only to the growing fraction.

The Effect of Cell Death on Fluorescence Kinetics

Let us now consider the case where cell death is appreciable and dye transfer to the live cells occurs rapidly. The kinetics of cell death are represented in equation 10.

$$(dN(t)/dt)_1 = BN(t) \qquad (10)$$

Above, B is the proportionality constant relating the rate of loss of cells from the population to the size of the population. The derivative is subscripted; the 1 corresponds to the process of cell death. Let us rewrite equation 3 in a similar fashion.

$$(dN(t)/dt)_2 = AN(t) \qquad (3)$$

Here, the 2 corresponds to the process of cell growth. Combining the growth and death processes gives, $$dN(t)/dt = (dN(t)/dt)_1 + (dN(t)/dt)_2. \qquad (11)$$

This equation is simply the result of the superposition of two independent processes. By substitution, it follows that, $$dN(t)/dt = (A + B)N(t) \qquad (12)$$

By analogy to equations 4 to 6, this equation reduces to, $$N(t) = N_o \exp((A+B)t). \qquad (13)$$

A was determined in equation 7 to be $0.693/T_2$. In a similar fashion, B can be shown to be equal to $-0.693/T_{\frac{1}{2}}$. The negative sign corresponds to the fact that cell death is a decay process. Likewise, $T_{\frac{1}{2}}$ now represents a decay constant which we will call the average cell half-life in the population. By substitution, equation 13 becomes, $$N(t) = N_o \exp((0.693/T_2 - 0.693/T_{\frac{1}{2}})t) \qquad (14)$$

By combining equations 3 and 14, we can solve for the fluorescence kinetics.

$$F(t) = F_o \exp((0.693/T_{\frac{1}{2}} - 0.693/T_2)t) \qquad (15)$$

In the above equation, we can combine the constants $T_2$ and $T_{\frac{1}{2}}$ as shown below.

$$1/T_D = 1/T_2 - 1/T_{\frac{1}{2}} \qquad (16)$$

Incorporating the relationship in equation 16 into equations 14 and 15 gives the cell and fluorescent kinetic equation listed below.

$$N(t) = N_o \exp(0.693 t/T_D) \qquad (17a)$$

$$F(t) = F_o \exp(-0.693 t/T_D) \qquad (17b)$$

Figure 4:
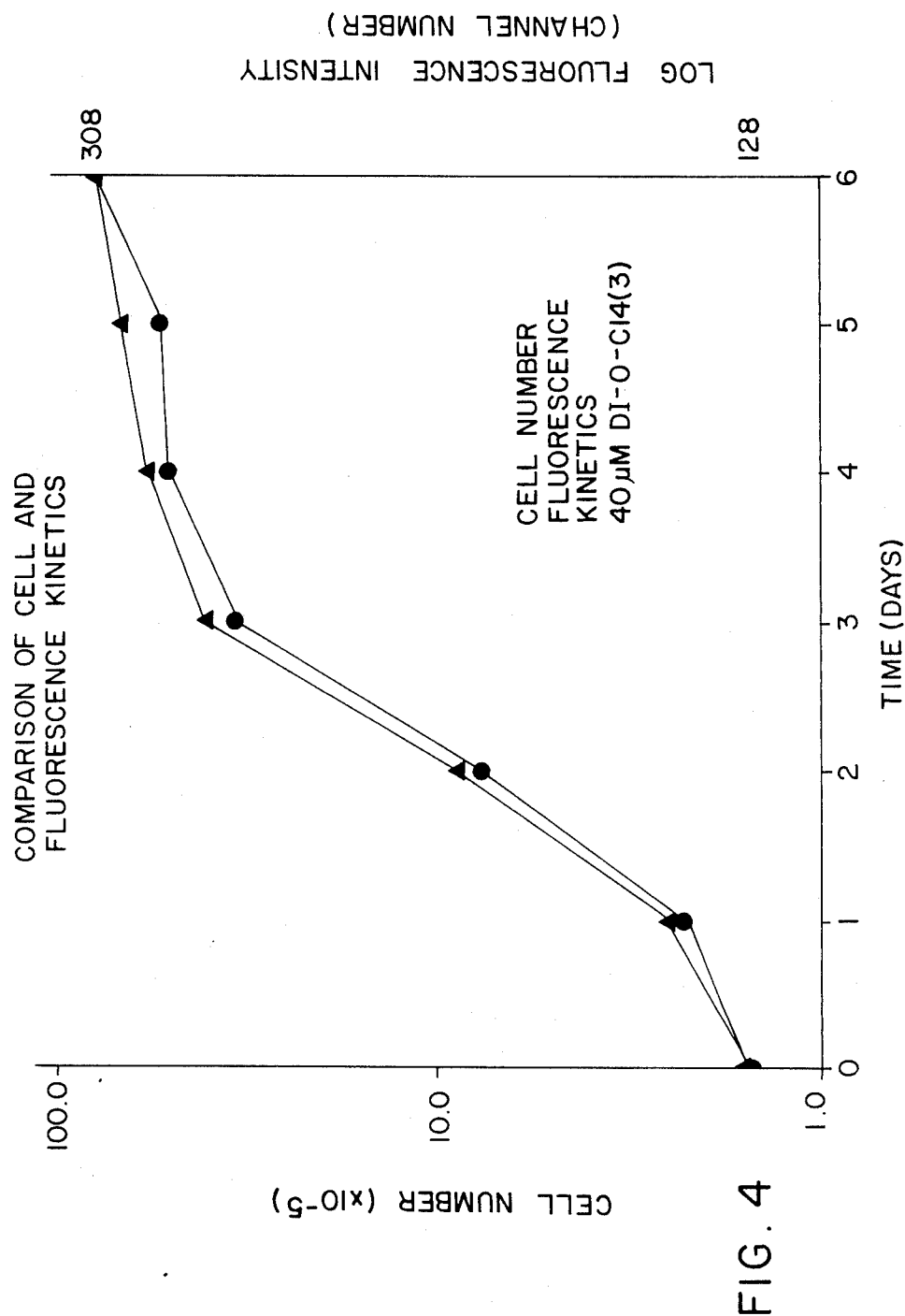
FIG. 4 is a graph comparing cell and fluorescence kinetics.

In equations 17a and 17b, the parameter, $T_D$, has the units of time and represents the actual cell doubling time rather than the cell cycle time. Equation 17b will define the fluorescence distribution in a culture where cell death is significant and dye reabsorption is rapid. If either of these conditions is not met, then equation 9 applies. A comparison of equations 17a and 17b shows that the cell and fluorescence kinetics are inversely related, such that a plot of the cell growth curve and the inverse of the fluorescence kinetics curve can be superimposed. This fact was clearly demonstrated in FIG. 4.

Incorporation of a Cell Growth Lag Time

Let us now assume that there is a lag time when the cells are put into culture. Let us also simplify the treatment by further assuming that the population will go from a growth rate of zero to its maximum rate in one step. Under these conditions, it can readily be shown that the relationship defining cell growth is, $$N(t) = N_o \quad t \geq t_L \qquad (18a)$$

$$N(t) = N_o \exp(0.693(t - t_L)/T_D) \quad t < t_L \qquad (18b)$$

Here, $t_L$ is defined as the lag time. Combining equation 3 with the above relationships gives, $$F(t) = F_o \quad t \geq t_L \qquad (19a)$$

$$F(t) = F_o \exp(-0.693(t - t_L)/T_D) \quad t < t_L \qquad (19b)$$

Using these equations, both the doubling time and the lag time can be determined by knowing $F_o$ and by determining F(t) at three or four times during exponential growth.

Determination of the Growing Fraction

Let us consider the case where a fraction of the population is not growing. Initially let us assume there is no lag time. We will add back a lag time later. For the purpose of this derivation a definition is needed. In equation 21, $$N_o = (N_o)_g + (N_o)_n \qquad (20)$$

The subscripts g and n refer to the growing and non-growing fractions, respectively. At any time, t, the number of cell in the population will be the sum of the growing and non-growing populations.

$$N(t) = (N_o)_n + (N_o)_g \exp(0.693t/T_D) \quad (21)$$

However, this equation cannot be substituted into equation 3 as we have previously done. In this case, the growing and non-growing fractions must be handled separately. For this purpose, equation 3 must be rewritten, as shown.

$$F(t) = (F_o)_n(N_o)_n(1/N(t))_n + (F_o)_g(N_o)_g(1/N(t))_g \quad (22)$$

In equation 22, $(1/N(t))_n$ is equal to $(1/(N_o)_n)$. Therefore, the equation reduces as shown below.

$$F(t) = (F_o)_n + (F_o)_g(N_o)_g(1/N(t))_g \quad (23)$$

$$F(t) = (F_o)_n + (F_o)_g \exp(-0.693t/T_D) \quad (24)$$

We can also introduce a lag time by analogy to equation 19b.

$$ti \, F(t) = (F_o)_n + (F_o)_g \exp(-0.693(t-t_L)/T_D) \quad (25)$$

The fraction of growing cells in the population can be determined using equation 25. The determination is more complex than in previous cases because sub-populations are involved. To determine the growing fraction, one must wait until the sub-populations are distinguishable. At this point, the fluorescence intensity of the non-growing fraction can be determined directly. An extrapolation of the change in fluorescence intensity over time of the growing fraction to time zero allows one to calculate the fluorescence intensity of the growing fraction at zero time. The growing fraction is then simply the ratio of the fluorescence intensity of the growing fraction at zero time to the total population fluorescence intensity.

The preferred embodiments of the invnention are illustrated by the above, however, the invention is not limited to the instructions disclosed herein, and all rights to all modifications within the scope of the following claims is reserved.

What is claimed is:

1. A method for determining cell growth rate that comprises measuring changes in levels of cyanine dye in the plasma membranes of daughter cells derived from parent cells labelled with a cyanine dye wherein fluorescence is used to measure changes in levels of cyanine dye.

2. A method of claim 1 wherein the cells are tissue culture cells.

3. A method of claim 2 wherein the cells are human tumor cells.

4. A method of claim 3 wherein the human tumor cells are grown in media containing cancer therapeutic agents so that tumor cell sensitivity to these agents is determined.

5. A method of claim 2 wherein the cells are white blood cells.

6. The method claim 2 wherein the cyanine dye is $DiSC_{14}(5)$ or $DiOC_{14}(3)$.

7. A method of claim 1 wherein the cells are bacteria.

8. A method of claim 7 wherein the bacteria are grown in media containing antibacterial agents so that bacterial sensitivity to these agents is determined.

9. A method of claim 8 wherein the cyanine dye is $DiSC_{14}(5)$ or $DiOC_{14}(3)$.

10. A method of claim 1 wherein the cells are yeast.

11. A method of claim 1 wherein the yeast are grown in media containing antifungal agents so that sensitivity to these agents can be determined.

12. A method of claim 11 wherein the cyanine dye is $DiSC_{14}(5)$ or $DiOC_{14}(3)$.

13. A method of claim 1 wherein the cells are in vivo tissue cells.

14. A method of claim 13 wherein the in vivo tissue cells are transplanted cells.

15. A method of claim 14 wherein the transplanted cells are bone marrow cells.

16. A method of claim 13 wherein the in vivo tissue cells are corneal epithelial cells.

17. A method of claim 1 wherein the cyanine dye is $DiSC_{14}(5)$ or $DiOC_{14}(3)$.

18. A method of claim 1 wherein the cyanine dye absorbs light at a wavelength greater than 680 nm.

19. A method of claim 16 wherein the cyanine dye absorbs light at a wavelength greater than 680 nm.

* * * * *